(12) United States Patent
Howell et al.

(10) Patent No.: US 6,184,187 B1
(45) Date of Patent: Feb. 6, 2001

(54) PHOSPHORUS COMPOUNDS AND THEIR USE AS CORROSION INHIBITORS FOR PERFLUOROPOLYETHERS

(75) Inventors: Jon L. Howell, Bear, DE (US); Michael A. Hofman, State College, PA (US)

(73) Assignee: E. I. duPont de Nemours and Company, Wilmington, DE (US)

( * ) Notice: Under 35 U.S.C. 154(b), the term of this patent shall be extended for 0 days.

(21) Appl. No.: 09/056,085

(22) Filed: Apr. 7, 1998

(51) Int. Cl.$^7$ .................................................. C10M 131/06
(52) U.S. Cl. ......................... 508/427; 508/588; 558/194; 558/195; 558/203; 558/204; 558/207
(58) Field of Search .................................. 508/427, 588; 558/203, 204, 207, 194, 195

(56) References Cited

U.S. PATENT DOCUMENTS

| | | | |
|---|---|---|---|
| 3,083,224 | 3/1963 | Brace et al. | 260/461 |
| 3,306,855 | 2/1967 | Borecki | 508/427 |
| 3,308,207 | 3/1967 | Christian et al. | 260/953 |
| 3,308,208 * | 3/1967 | Christian et al. | 260/955 |
| 3,337,655 | 8/1967 | Christian et al. | 260/955 |
| 3,412,181 * | 11/1968 | Braun | 260/955 |
| 3,567,802 | 3/1971 | Garth | 260/950 |
| 3,899,366 | 8/1975 | Tajkowski | 148/6.16 |
| 4,877,815 * | 10/1989 | Buckmaster | 521/85 |
| 5,132,446 | 7/1992 | Tohzuka et al. | 558/186 |
| 5,376,289 | 12/1994 | Montagna et al. | 508/427 |
| 5,442,084 * | 8/1995 | Lal | 558/141 |
| 5,550,277 * | 8/1996 | Paciorek et al. | 558/194 |

FOREIGN PATENT DOCUMENTS

| | | |
|---|---|---|
| 0 605 403 A2 | 7/1994 | (EP) . |
| 255269 | 3/1970 | (RU) . |
| 1810382 A1 | 4/1993 | (RU) . |

OTHER PUBLICATIONS

Pavlenko: Esters of bis(perfluoroalkyl)phossphinic acids; J. Gen. Chem. USSR; vol. 59. No. 3; Aug. 20, 1989.

\* cited by examiner

*Primary Examiner*—Margaret Medley
*Assistant Examiner*—Cephia D. Toomer
(74) *Attorney, Agent, or Firm*—Lucas K. Shay

(57) ABSTRACT

Novel phosphorus compounds are effective corrosion inhibitors for perfluoropolyether lubricating oils and greases, and hydraulic fluids.

29 Claims, No Drawings

PHOSPHORUS COMPOUNDS AND THEIR USE AS CORROSION INHIBITORS FOR PERFLUOROPOLYETHERS

BACKGROUND OF THE INVENTION

1. Field of Invention

This invention relates to novel organic phosphorus compounds. The compounds have general utility as surfactants and particular utility as an additive to perfluoropolyether compositions, including oil and grease lubricants, to inhibit corrosion and rust of metals in contact with the compositions.

2. Description of Related Art

Perfluoropolyethers have excellent thermal and oxidative stability and are used as greases, hydraulic fluids, and oils for service under extreme or demanding conditions wherein more conventional oils and greases are not adequate, for instance at temperatures above 260° C. and up to 370° C. to 425° C., depending on the particular oil or grease. These oils and greases are available from a number of commercial sources, including E. I. du Pont de Nemours that markets them under the Krytox® trademark.

While the perfluoropolyethers per se are highly stable, they are highly permeable to oxygen and moisture. Thus, the oil and grease do not form an effective barrier against rust and corrosion of metallic parts they contact. As used herein, the term "corrosion" refers to the oxidation of metal in contact with oxygen, and the term "rust" refers to the oxidation of metal in contact with water.

Sodium nitrite conventionally has been added as a corrosion inhibitor to some perfluoropolyether greases. Sodium nitrite is not soluble in perfluoropolyether oils. In the greases, it is present as a particulate dispersion. Ideally, a rust and corrosion inhibitor would be present in solution to provide better protection and to eliminate the potential problem of separation from the oil or grease.

Many organic phosphorus compounds have been suggested in the patent literature as rust and/or corrosion inhibitors for perfluoropolyether oils and greases. For example, U.S. Pat. No. 3,306,855 to Borecki proposes a perfluoroalkyl ether phosphate containing at least one acidic hydrogen, and U.S. Pat. No. 5,550,277 to Paciorek et al., proposes a variety of fully and partially esterified phosphates and phosphates, some of which are acidic.

Other candidate rust and corrosion inhibitors proposed in the art are very difficult or expensive to synthesize. For example, some of the proposed additives contain large quantities of costly perfluoroalkyl substituents. Others, such as some of the partially esterified phosphates proposed by U.S. Pat. No. 5,550,277, require formation of an intermediate fluoroether-substituted phenol that is very difficult to synthesize in a commercial manufacturing process.

The use of acidic rust and corrosion inhibitors is contraindicated in admixture with perfluoropolyether greases containing the common sodium nitrite inhibitor, since the acidic group may react with the sodium nitrite to generate noxious nitrogen oxides. Since the presence of greases containing sodium nitrite inhibitors has been pervasive, and they are expensive to replace, there is a high probability that new greases and oils will be placed in existing equipment lubrication reservoirs containing sodium nitrite.

Thus, there is an ongoing need for new corrosion and rust inhibitor additives for perfluoropolyether compositions, including oils and greases.

SUMMARY OF THE INVENTION

This invention provides novel partially and fully esterified aryl phosphorus compounds that are (i) soluble or form stable dispersions in perfluoropolyethers, or (ii) compatible with sodium nitrite present in many commercial perfluoropolyether greases. The novel compounds provide excellent rust and corrosion resistance to metals that contact the perfluoropolyether. The compounds are readily synthesized and relatively inexpensive in that some of the perfluoroalkyl substition in prior art compounds is replaced with aryl and aryloxy substituents, providing the desired functionality of prior additives with less expensive substituents. More particularly the invention provides:

Class A: A perfluoroether- and phosphorus-containing compound selected from the group consisting of partially esterified aryl phosphates, or aryl phosphonates, and salts thereof, containing either (i) a mono- or poly-alkylene oxide linking group between the phosphorus and a fluorocarbon group, or (ii) no linking group between the phosphorus and fluorocarbon group;

Class B: Asymmetrical perfluoroether- and phosphorus-containing compounds being either (i) aryl phosphites or phosphates containing a mono or poly alkylene oxide linking group between the phosphorus and a perfluoroether group, or (ii) aryl phosphines, phosphinites, phosphonites, phosphine oxides, phosphinates or phosphonates with no linking group between the phosphorus and a fluorocarbon group; and Class C: Salts of partially esterified aryl phosphates having an aryl group between the phosphorus and a fluorocarbon.

These novel compounds have general utility as surfactants, and particular utility as corrosion and rust inhibitors in perfluoropolyether compositions such as oils and greases.

DETAILED DESCRIPTION OF THE INVENTION

The novel phosphorus compounds of the invention are represented by the following definitions:

Class A: A perfluoroether- and phosphorus-containing compound selected from the group consisting of partially esterified aryl phosphates, or aryl phosphonates, and salts thereof, containing either (i) a mono- or poly-alkylene oxide linking group between the phosphorus and a fluorocarbon group, or (ii) no linking group between the phosphorus and fluorocarbon group;

Class B: Asymmetrical perfluoroether- and phosphorus-containing compounds being either (i) aryl phosphites or phosphates containing a mono or poly alkylene oxide linking group between the phosphorus and a perfluoroether group, or (ii) aryl phosphines, phosphinites, phosphonites, phosphine oxides, phosphinates or phosphonates with no linking group between the phosphorus and a fluorocarbon group; and Class C: Salts of partially esterified aryl phosphates having an aryl group between the phosphorus and a fluorocarbon.

Specific compounds within the three classes will be described first. Then, convenient synthesis techniques will be described.

CLASS A:

Representative compounds within Class A have the following formulae:

Class A(i) compounds having a mono or poly alkylene oxide linking group:

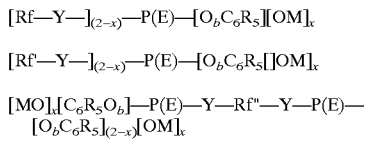

(Formula I)
(Formula II)
(Formula III)

where:
Y is $(CH_2)_zO(CH_2CH_2O)_{z'}$, wherein z is 1 to 4 and z' is 0, 1 or 2,
x is 0.05 to 1,
E is oxygen or sulfur,
b is 0 or 1,
R is the same or different substituent chosen from hydrogen, halogen, alkyl, aryl, nitro, cyano, alkoxy, primary and secondary amino, sulfonyl, carboxyl, or phenoxy, and
M is hydrogen, alkali metal, alkaline earth metal, or ammonium.
Rf is a polyether chain having a molecular weight ranging from 400 to 15,000 and composed of repeating units selected from the group consisting of:

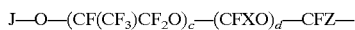

where:
J is a fluoroalkyl group selected from the group consisting of $-CF_3$, $-C_2F_5$, $-C_3F_7$, $-CF_2Cl$, $-C_2F_4Cl$, and $-C_3F_6Cl$,
X is $-F$ or $-CF_3$,
Z is $-F$, $-Cl$ or $-CF_3$, and
c and d are numbers such that the c/d ratio ranges from 0.01 to 0.5, and the molecular weight ranges from 400 to 15,000;

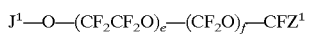

where:
$J^1$ is a fluoroalkyl group selected from the group consisting of $-CF_3$, $-C_2F_5$, $-CF_2Cl$, and $-C_2F_4Cl$,
$Z^1$ is $-F$ or $-Cl$, and
e and f are numbers such that the e/f ratio ranges from 0.5 to 2 and, the molecular weight ranges from 400 to 15,000;

where:
J and X are as defined above,
Z is $-F$, $-Cl$, or $-CF_3$, and
g, h and i are numbers such that (g+h) ranges from 1 to 50, the i/(g+h) ratio ranges from 0.1 to 0.05, and the molecular weight is from 400 to 15,000;

where:
$J^2$ is $-C_2F_5$ or $-C_3F_7$, and
j is a number such that the molecular weight ranges from 400 to 15,000;

where:
$J^3$ is selected from the group consisting of $-CF_3$, $-C_2F_5$, and $-C_3F_7$,
Q and $Z^2$, equal or different, are F, Cl or H, and k is a number such that the molecular weight ranges from 400 to 15,000; and

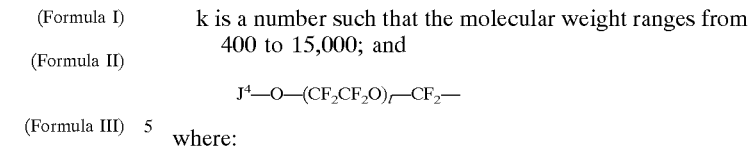

where:
$J^4$ is $-CF_3$, or $-C_2F_5$ and
l is a number such that the molecular weight ranges from 400 to 15,000; or $Z^2-(CF_2)_m$ where:
$Z^2$ is H, F, or Cl and
m has a value from 2 to 20; or
Rf" is a perfluoropolyether chain having a number average molecular weight of 500 to 15,000, selected from the group consisting of:

$(CF_2CF_2O)_n-(CF_2O)_o-CF_2-$     (i)

wherein the units with formulae $C_2F_4O$ and $CF_2O$ are randomly distributed along the chain, and n and o are integers, whose ratio, n/o, is in the range of from 0.3 to 5;

$(C_3F_6O)_p-(CF_2CF_2O)_q-(CFXO)_r-CF_2-$     (ii)

wherein
X is F or $CF_3$ and
p, q and r are numbers such that (p+q) ranges from 1 to 50, and the r/(p+q) ratio ranges from 0.1 to 0.05, and the molecular weight is from 400 to 15,000; and $-((CQZ^2)CF_2CF_2O)_s-CF_2-CF_2-$     (iii)

where
Q and $Z^2$, equal or different, are F, Cl or H, and
s is a number such that the molecular weight ranges from 400 to 15,000.

Representative compounds within Class A(i) include:
For Formula I;

$F(CF(CF_3)CF_2O)_nCF(CF_3)CH_2OP(O)[OH]C_6H_5$ and $F(CF(CF_3)CF_2O)_nCF(CF_3)CH_2OP(O)[OH]OC_6H_5$ where n is 4 to 10.
For Formula II;

$F(CF_2)_mCH_2CH_2OP(O)[OH]C_6H_5$ and $F(CF_2)_mCH_2CH_2OP(O)[OH]OC_6H_5$ where m is 4, 6 or 8.
For Formula III;

$[HO](C_6H_5)P(O)OCH_2-(CF_2CF_2O)_n-(CF_2O)_o-CF_2-CH_2OP(O)(C_6H_5)[OH]$ and $[HO](H_5C_6O)P(O)OCH_2-(CF_2CF_2O)_n-(CF_2O)_o-CF_2-CH_2OP(O)(OC_6H_5)[OH]$ where (n+o)=8 and n/o=1.
Class A(ii) compounds having a mono or poly alkylene oxide linking group:

$$[Rf—]_{(2-x)}—P(E)—[O_b—C_6R_5][OM]_x \quad \text{(Formula IV)}$$

$$[Rf'—]_{(2-x)}—P(E)—[O_bC_6R_5][OM]_x \quad \text{(Formula V)}$$

$$[MO]_x[C_6R_5O_b]_{(2-x)}—P(E)—Rf''—P(E)—[O_bC_6R_5]_{(2-x)}[OM]_x \quad \text{(Formula VI)}$$

wherein Rf, Rf', Rf", x, E, b, R, and M are as previously defined for Formulae I to III.

Representative compounds within Class A(ii) include:

For Formula IV;

$$F(CF(CF_3)CF_2O)_nCF(CF_3)P(O)[OH]C_6H_5$$

and $$F(CF(CF_3)CF_2O)_nCF(CF_3)P(O)[OH]OC_6H_5$$

where n is 4 to 10.

For Formula V;

$$F(CF_2)_mP(O)[OH]C_6H_5$$

and $$F(CF_2)_mP(O)[OH]OC_6H_5$$

where m is 4, 6 or 8.

For Formula VI;

$$[HO][(C_6H_5)P(O)—(CF_2CF_2O)_n—(CF_2O)_o—CF_2—P(O)(C_6H_5)[OH]$$

and $$[HO][(H_5C_6O)P(O)—(CF_2CF_2O)_n—(CF_2O)_o—CF_2—P(O)(OC_6H_5)[OH]$$

where (n+o) is 8, and n/o is 1

CLASS B:

Representative compounds within Class B have the following formulae:

Class B(i) compounds having a mono or poly alkylene oxide linking group:

$$[Rf—Y—]_{(3-y)}—P(E)_a—[O—C_6R_5]_y \quad \text{(Formula VII)}$$

$$(C_6R_5O)_2—P(E)_a—Y—Rf''—Y—P(E)_a—(OC_6R_5)_2 \quad \text{(Formula VIII)}$$

wherein R, Rf, Y, and E are as previously defined and y is 0.05 to 2, and a is 0 or 1.

Representative compounds within Class B(i) include:

For Formula VII;

$$[F(CF(CF_3)CF_2O)_nCF(CF_3)CH_2O]P(OC_6H_5)_2$$

and $$[F(CF(CF_3)CF_2O)_nCF(CF_3)CH_2O]_2P(O)(OC_6H_5)$$

where n is 4 to 10.

For Formula VIII;

$$(H_5C_6O)_2P—(CF_2CF_2O)_n—(CF_2O)_o—CF_2—P(OC_6H_5)_2$$

and $$(H_5C_6O)P(O)—(CF_2CF_2O)_n—(CF_2O)_o—CF_2—P(O)(OC_6H_5)_2$$

where n is (n+o) is 8, and n/o is 1.

Class B(ii) compounds not having a polyalkylene oxide linking group:

$$[Rf—]_{(3-y)}—P(E)_a—[O_bC_6R_5]_y \quad \text{(Formula IX)}$$

$$[Rf']_{(3-y)}—P(E)_a—[O_bC_6R_5]_y \quad \text{(Formula X)}$$

$$[C_6R_5O]_2—P(E)_a—Rf''—P(E)_a—[O—C_6R_5]_2 \quad \text{(Formula XI)}$$

wherein

Rf, Rf', Rf", a, b, E, R, y, and n are as previously defined for Formulae I to VIII.

Representative compounds within Class B(ii) include:

For Formula IX;

$$F(CF(CF_3)CF_2O)_nCF(CF_3)P(C_6H_5)_2$$

$$[F(CF(CF_3)CF_2O)_nCF(CF_3)]_2P(OC_6H_5)$$

$$[F(CF(CF_3)CF_2O)_nCF(CF_3)]P(O)(C_6H_5)_2$$

$$[F(CF(CF_3)CF_2O)_nCF(CF_3)]_2P(O)(OC_6H_5)$$

where n is 4 to 10.

For Formula X;

$$F(CF_2)_mP(C_6H_5)_2$$

$$[F(CF_2)_m]_2P(OC_6H_5)$$

$$F(CF_2)_mP(OC_6H_5)_2$$

$$[F(CF_2)_m]P(O)(C_6H_5)_2$$

$$[F(CF_2)_m]_2P(O)(OC_6H_5)$$

$$F(CF_2)_mP(O)(OC_6H_5)_2$$

where m is 4,6 or 8.

For Formula XI;

$$(H_5C_6)_2P—(CF_2CF_2O)_n—(CF_2O)_o—CF_2—P(C_6H_5)_2$$

$$(H_5C_6O)_2P—(CF_2CF_2O)_n—(CF_2O)_o—CF_2—P(OC_6H_5)_2$$

$$(H_5C_6)_2P(O)—(CF_2CF_2O)_n—(CF_2O)_o—CF_2—P(O)(C_6H_5)_2$$

$$(H_5C_6O)_2P(O)—(CF_2CF_2O)_n—(CF_2O)_o—CF_2—P(O)(OC_6H_5)_2$$

where (n+o) is 8; and n/o is 1.

CLASS C:

Representative compounds within Class C have the following formulae:

$$[Rf'''—C_6R_4—O]_{(3-u-w)}—P(E)-[O_b—C_6R'_5]_w[OM']_u \quad \text{(Formula XII)}$$

wherein

Rf''' is Rf' or Rf", and Rf, Rf", E, b, and R are as previously defined for Formulae I to III.

M' is an alkali metal, alkaline earth metal, or ammonium, and u and w are the same or different between 0 and 1, and R' is an aryl group.

Examples of R groups include phenyl and substituted phenyl, $C_6H_4—R''$, in which R" is an aromatic, alkyl, or thioaryl ($SC_6H_5$).

SYNTHESIS

Compounds of Class A(i) and B(i)

Syntheses of the additives of the invention are accomplished by the method described by Moreton in U.S. Pat. No. 2,694,083 by reaction of either (a) aryloxy substituted or aryl substituted phosphorus oxychlorides at elevated temperatures with a fluoroalcohol of the formula Rf—OH, or (b)

with the corresponding fluoroalkyl phosphorus dichloride and a substituted phenol. Alternately, the products are prepared by mixing said reactants in the presence of a dry aprotic organic base such as triethylamine or pyridine, and allowing the reaction to proceed at room temperature until complete either with or without solvent as described by Paciorek in U.S. Pat. No. 5,550,277. Control over the specific reaction products is by stoichiometry. This reaction is followed by hydrolysis to form the corresponding acid ester. Additionally, the products are neutralized with a solution or suspension of the hydroxide or carbonate of the alkali metal or alkaline earth metal, or ammonium hydroxide solution, prior to isolation to provide the corresponding salt, producing a rust and corrosion prevention additive compatible with perfluoropolyether oils and greases containing sodium nitrite. The solution is washed with water to remove excess acid and salts or base and salts, then vacuum stripped to remove solvents and volatiles.

Compounds of Class A(ii) and B(ii)

Those compounds are prepared by reacting a perfluoro alkyl or perfluoroether iodide with elemental phosphorus at elevated temperatures. The isolated diiodo phosphine can either be reacted with a metalated aryl or aryloxy compound preparing the corresponding phosphorus(III) compounds. Oxidation with chlorine/water or hydrogen peroxide gives the phosphorus(V) oxide. Oxidation of the phosphorus(III) with chlorine followed by treatment with $H_2S$ or $Na_2S$ gives the thiophosphorus(V) materials.

Compounds of Class C

Syntheses of the perfluoropolyether additives of Formula XI and XII are accomplished as described by Paciorek et al. in U.S. Pat. No. 5,550,277 cited above, except that the final products of Paciorek et al. are neutralized with a solution of suspension of the hydroxide or carbonate of the alkali metal or alkaline earth metal, or ammonium hydroxide solutions prior to isolation to provide the corresponding salt, producing a rust and corrosion prevention additive compatible with perfluoropolyether oils and greases containing sodium nitrite.

USE OF THE PHOSPHORUS COMPOUNDS AS RUST AND CORROSION INHIBITORS

The phosphorus compounds of the present invention constitute new anticorrosion and antirust additives effective in all perfluoropolyether lubricants. These new additives are variously soluble or dispersible in the perfluoropolyether oil and provide antirust and anticorrosion protection to the oil thereby improving wear of parts lubricated or in contact with the oil. The alkali metal, alkaline earth metal, or ammonium salts of the partially esterified phosphorus compound additives either allow sodium nitrite to be replaced or, since they are compatible with the sodium nitrite, provide the option to retain sodium nitrite in the formulation. The present invention further provides perfluoropolyether oils, greases, and fluids containing an effective amount of the inhibitor.

By the term "effective amount" is meant the amount required to produce a useful level of inhibition for the required service life of the device containing the oil or grease at the operating temperature. Various metals differ considerably in the amount of corrosion and rust that will occur and the amount of inhibitor required to prevent it. Longer service life, higher service temperatures, and higher molecular weight phosphorus-containing additives may require larger amounts of the inhibitor. In practice, this typically corresponds to a concentration of from 0.1 to 10.0% by weight, and preferably 1.0 to 3.0% by weight, of the anticorrosion and antirust additives of this invention. So long as about 0.1% by weight of the inhibitor is present, a significant amount of corrosion and rust inhibition is obtained. As the amount of inhibitor is increased, decreasing corrosion and rusting occurs up to about a 2% concentration of the inhibitor. Concentrations higher than about 2% seldom produce any increase in effect. The additive may be added at the point of use, but is preferably added during manufacture or packaging of the perfluoropolyether fluid, when appropriate quality control is more likely to be available.

Representative perfluoropolyethers having neutral end groups, utilizable for the formulation of oils and greases are available on the market under the trade-names FOMBLIN (from Ausimont, Milan, Italy), KRYTOX (from E. I. du Pont de Nemours and Company, Wilmington, Del.), and DENUM (from Daikin, Osaka, Japan).

A grease based on perfluoropolyethers is typically composed of 15% to 40% by weight of polytetrafluoroethylene, which acts as a thickening agent, and 60% to 85% by weight of a liquid perfluoropolyether, together with minor amounts of other products, such as perfluoroalkyl surfactants or polyoxyperfluoroalkyl surfactants, or other additives known in the art, such as stabilizers, anticorrosive agents, anti-wear agents etc. Additives of this type are also usually included in oils based on perfluoropolyethers.

Having described the invention, it will further be illustrated, but not limited, by the following examples.

EXAMPLES

MATERLALS

Phosphorus trichloride, phenylphosphonic dichloride, 4-nitrophenyl phosphorodichloridate, 4-chlorophenyl dichlorophosphate and the phenyl ester of phosphorodichloridic acid are available from chemical supply houses such as Aldrich Chemical Company, Milwaukee, Wis. Other phosphorus reagents can be prepared using the same techniques as described above.

Hexafluoropropylene oxide acid fluorides [$F(CF(CF_3)CF_2O)_nCF(CF_3)COF$]having n=1, 2, and 3 are available from PCR Inc., Gainesville, Fla., The trimer alcohol, $F[CF(CF_3)CF_2-O]_3CF(CF_3)CH_2OH$ is also available from PCR Inc. Other perfluoroalkyl ether based alcohols, such as Ausinont's MF402 for the monofunctional alcohol, and FOMBLIN Z-Dol, Z-Dol 4000, Z-Dol TX, are also available.

KRYTOX oils and greases are available from E. I. du Pont de Nemours and Company, Wilmington, Del. FOMBLIN Oils and Greases are available from Ausimont USA Inc., Thorofare, N.J. or Daiken Industries, Ltd., Chemical Division, Osaka, Japan.

Fluoroalcohols of the structure $F(CF_2)_q(CH_2)_2OH$ are available from E. I. du Pont de Nemours and Company as mixtures having q=2, 4, 6, 8, and 10 or as individual homologues following distillation.

TEST METHODS

Test Method 1

Rust/Corrosion Testing Procedure (ASTM (American Society for Testing Materials) D-665 Modified as described)

The coupons are cleaned in toluene or Stoddard solvent using a sonicator for 15 minutes. They are then stored in a sealed container filled with fresh solvent and soaked in a fluorochemical solvent such as VERTREL XF (1,1,1,2,3,4,4,5,5,5-decafluoropentane, available from E. I. du Pont de Nemours and Company, Wilmington, Del.) for at least 5 minutes. The coupon is then air-dried for 10 minutes.

Contamination before use is avoided. The coupons are coated thoroughly by dipping for 1 minute in the solution to be tested. Excess solution is allowed to drain for 1 hour. The coupons are placed into a beaker of medium hard water (see below) held at 80° C. The volume is adjusted to have the coupons half immersed in the solution. The test is continued for 24 hours, recording any rust formation. The test coupons are removed from the solution, wiped with a paper towel to remove loose rust, and given a final evaluation.

The test coupons are C1018 Centerless ground cylindrical coupons having ¼" diameter×2½" length (0.64 cm diameter and 6.35 cm length), with 1/16" slot (0.16 cm slot), part #2200 from Metal Samples Co., Munford Ala.

Medium hard water (MIL-I-25017E) is prepared using three stock solutions, 16.4 g/l sodium bicarbonate, 13.2 g/l anhydrous calcium chloride, and 8.2 g/l anhydrous magnesium sulfate. Sodium bicarbonate stock solution (10 ml) is pipetted into 800 ml distilled water in a one liter volumetric flask, and shaken vigorously. While swirling the contents of the flask, calcium chloride stock solution (10 ml) and then 10 ml of the magnesium sulfate stock solution are pipetted into the flask, distilled water is added to bring the volume to one liter, and the solution mixed thoroughly. The final blend shall be clear and free of precipitation.

Evaluations:

Excellent: no rust or light rust in a 24-hour period.

Good: moderate rust occurring in a 24-hour period.

Fair: severe rust occurring in a 24-hour period, but not covering over 35% of the surface of the specimen.

Poor: rust covering over 35% of the surface of the specimen (i.e., additive does practically nothing to prevent rust).

Results are shown in Table 1.

Test Method 2

Wear Testing (4-Ball, Cameron-Plint, and Load to Failure)

Wear testing was done in accordance with ASTM D-4172 for the 4-ball wear test and according to Cameron-Plint Tribology, Wokingharn, England, producers of the Cameron-Plint tester. The Load to Failure (Pin on V-Block) Test was run according to ASTM D-3233. Results are shown in Tables 2, 3, and 4.

Test Method 3

Oxidative Stability

The oxidative stability of the additive was tested using the Micro-Oxidation Test described in Tribology Transactions, V38(3), (1995), 618–626. Results are shown in Table 3.

EXAMPLES

Example 1a

Preparation of Methyl Ester

Into a 12-liter 3-neck flask fitted with a mechanical stirrer, thermocouple, and addition funnel is placed 1738.14 g of $F(CF(CF_3)CF_2O)_nCF(CF_3)COF$, having n=2 to 16. With cooling of the reactor, 347 g anhydrous methanol is added. A mildly exothermic reaction takes place and, after stirring for one hour, the methyl ester, $F(CF(CF_3)CF_2O)_nCF(CF_3)COOCH_3$, is washed with water to remove excess methanol and hydrogen fluoride. Final neutralization is effected by filtration through a column containing calcium carbonate and alumina. The yield is 1531 g of methyl ester.

Example 1b

Preparation of Perfluoroether Alcohol

Into a 5-liter 3-neck flask fitted with a mechanical stirrer, thermocouple, and addition funnel are placed 1569 g of isopropyl alcohol and 64.9 g of sodium borohydride. This mixture is cooled to 10° C. and 1568 g of the methyl ester, $F(CF(CF_3)CF_2O)_nCF(CF_3)COOCH_3$, prepared as in Example 1a, is added. The mixture is refluxed at 83° C. for 4 hours. After cooling to room temperature the excess sodium borohydride is decomposed with 20% ammonium chloride solution, washed with 10% saline and acetone, and dried to yield 1300 g of $F(CF(CF_3)CF_2O)nCF(CF_3)CH_2OH$, having n=2 to 16.

Example 1c

Preparation of Perfluoroether Phosphate

Into a 6-liter 3-neck flask fitted with a mechanical stirrer, thermocouple, and two addition funnels are placed 388.7 g of $C_6H_5OP(O)Cl_2$ and 1,000 ml of FREON 113 (1,1,2-trichlorotrifluoroethane). Simultaneously 2,000 g of the alcohol $F(CF(CF_3)CF_2O)_nCF(CF_3)CH_2OH$, prepared according to Example 1b, and 204.6 g of triethylamine are added to the flask while keeping the temperature below 15° C. After all of the reagents are added, the mixture is allowed to warm to room temperature and held at that temperature for 1 hour. Finally 5,000 g of water are introduced into the flask through an addition funnel and the mixture stirred for 4 hours. The product is washed with 2N dilute hydrochloric acid 3 times and then with sufficient acetone to break the emulsion. The mixture is split into 2 equal portions. Half was stored for use in Example 2. The solvent was removed from the remainder by vacuum distillation at 100° C. and 1 mm Hg pressure (133 Pa) to yield 1050 g of product. Multi-nuclear NMR analysis shows the compound to be $F(CF(CF_3)CF_2O)_nCF(CF_3)CH_2OP(O)[OH]OC_6H_5$.

Example 2

Preparation of Sodium Perfluoroether Phosphate $F(CF(CF_3)CF_2O)_nCF(CF_3)CH_2OP(O)[OH]OC_6H_5$, 1050 g, prepared according to Example 1c, was placed in a 2-liter 3-neck flask fitted with a mechanical stirrer and thermocouple. To this mixture is added sufficient saturated sodium carbonate solution to insure the mixture has a pH>7. The product is washed 3 times with water to remove base and salt and the solvent removed as above. Multi-nuclear NMR and elemental analysis shows the compound to be $F(CF(CF_3)CF_2O)_nCF(CF_3)CH_2OP(O)[ONa]OC_6H_5$.

Example 3

Preparation of Perfluoroether Phosphate

Into a 1.5-liter 3-neck flask fitted with a mechanical stirrer, thermocouple, and two addition funnels are placed 13.26 g of phenylphosphonic dichloride and 50 ml of FREON 113 (1,1,2-trichlorotrifluoroethane). After cooling with an ice water bath, 100 g of alcohol prepared according to Example 1b is added simultaneously with 7.21 g of triethylamine, keeping the temperature below 15° C. After all of the reagents are added, the mixture is allowed to warm to room temperature and held at that temperature for 1 hour. Finally 1,000 g of water are introduced into the flask through an addition funnel and the mixture stirred for four hours. The product is washed with a mixture of 1% saline and acetone. Product, 103 g, was recovered. Multi-nuclear NMR analysis following solvent removal shows the compound to be $F(CF(CF_3)CF_2O)nCF(CF_3)CH_2OP(O)[OH][C_6H_5]$.

Example 4

Preparation of Sodium Perfluoroether Phosphate

Into a 100-milliliter 3-neck flask fitted with a mechanical stirrer, are placed 20.0 g of $F(CF(CF_3)CF_2O)_nCF(CF_3)CH_2OP(O)[OH][C_6H_5]$, prepared according to Example 3, along with 20 ml of FREON 113 (1,1,2- trichlorotrifluoroethane). To this mixture is added sufficient 1 M saturated sodium carbonate solution to insure the mixture has a pH greater than 7. The product is washed 3 times with water to remove base and salt and the solvent removed as above. Multi-nuclear NMR and elemental analysis following solvent removal shows the compound to be $F(CF(CF_3)CF_2O)_nCF(CF_3)CH_2OP(O)[ONa][C_6H_5]$.

Example 5
Preparation of Perfluoroether Phosphate with Aryl Substituent ($NO_2$)

Into a 200-milliliter 3-neck flask fitted with a mechanical stirrer, thermocouple, and two addition funnels are placed 12.05 g of 4-nitrophenyl phosphorodichloridate and 75 ml of FREON 113 (1,1,2-trichlorotrifluoroethane). After cooling with an ice water bath, 50 g of the alcohol $F(CF(CF_3)CF_2O)_nCF(CF_3)CH_2OH$, prepared according to Example 1b, is added followed by 4.03 g of pyridine while keeping the temperature below 15° C. After all of the reagents are added, the mixture is allowed to warm to room temperature and held at that temperature for 1 hour. Finally 500 g of water are introduced into the flask through an addition funnel and the mixture stirred for four hours. The product is washed with a mixture of 1% saline and acetone. Multi-nuclear NMR analysis analysis following solvent removal shows the compound to be $F(CF(CF_3)CF_2O)_nCF(CF_3)CF_2OP(O)[OH][p-OC_6H_4NO_2]$.

Example 6
Preparation of Perfluoroether Phosphate with Pentafluorophenyl Ester Group Into a 250-milliliter 3-neck flask fitted with a mechanical stirrer, thermocouple, and addition funnel are placed 9.02 g pentafluorophenol, 7.52 g phosphorus oxychloride and 75 ml FREON 113 (1,1,2-trichlorotrifluoroethane). After cooling the mixture with an ice water bath, 3.87 g of pyridine is slowly added to the flask, the product stirred for 1 hour, and warmed to room temperature. Then 50 g of the alcohol $F(CF(CF_3)CF_2O)_nCF(CF_3)CH_2OH$, prepared according to Example 1b, is added, followed by 4.03 g of pyridine, while keeping the temperature below 15° C. After all of the reagents are added, the mixture is allowed pentafluorophenyl to warm to room temperature and held at that temperature for 1 hour. Finally 500 g of water are introduced into the flask through an addition funnel and the mixture stirred for four hours. The product is washed with a mixture of 1% saline and acetone. Multi-nuclear NMR analysis following solvent removal shows the compound to be $F(CF(CF_3)CF_2O)_nCF(CF_3)CH_2OP(O)[OH][OC_6F_5]$.

Example 7
Preparation of Perfluoroether Phosphate with Aryl Substituent (Cl)

Into a 200-milliliter 3-neck flask fitted with a mechanical stirrer, thermocouple, and two addition funnels are placed 11.44 g of p-chlorophenyl dichlorophosphate and 75 ml of FREON 113 (1,1,2-trichlorotrifluoroethane). After cooling with an ice water bath, 50 g of the alcohol $F(CF(CF_3)CF_2O)_nCF(CF_3)CH_2OH$, prepared according to Example 1b, is added followed by 4.03 g of pyridine while keeping the temperature below 15° C. After all of the reagents are added, the mixture is allowed to warm to room temperature and held at that temperature for 1 hour. Finally 500 g of water are introduced into the flask through an addition funnel and the mixture stirred for four hours. The product is washed with a mixture of 1% saline and acetone. Multi-nuclear NMR analysis following solvent removal shows the compound to be $F(CF(CF_3)CF_2O)_nCF(CF_3)CH_2OP(O)[OH][p-OC_6H_4Cl]$.

Example 8
Preparation of Perfluorohexylethyl Phosphate

Into a 100-milliliter 3-neck flask fitted with a mechanical stirrer, thermocouple, and an addition funnel are placed 26.59 g of phenyl dichlorophosphate and 50 g 1H,1H,2H,2H-perfluorooctanol. After all of the reagents are added, the mixture is warmed about 130° C. to 150° C. for 16 hours and hydrogen chloride is evolved. Finally, following cooling to less than 50° C., 100 g of water are introduced into the flask through an addition funnel and the mixture heated to 95° C. for one hours. FREON 113 (1,1,2-trichlorotrifluoroethane) is introduced into the cooled flask and the product is washed with 2% saline and residual water removed at 100° C. and 1 mm Hg pressure (133 Pa). Multi-nuclear NMR analysis following solvent removal shows the compound to be $(C_6F_{13}CH_2CH_2O)_{1.2}P(O)[OH]_{0.8}[OC_6H_5]$.

Example 9
Preparation of a Fully Esterified Perfluoroether Phosphate

Into a 250-milliliter 3-neck flask fitted with a mechanical stirrer, thermocouple, and an addition funnel are placed 13.31 g of diphenyl chlorophosphate and 50 ml of FREON 113 (1,1,2-trichlorotrifluoroethane). After cooling with an ice water bath, 50 g of the alcohol, $F(CF(CF_3)CF_2O)_nCF(CF_3)CH_2OH$, prepared according to Example 1b, is added followed by 4.03 g of pyridine while keeping the temperature below 15° C. After all of the reagents are added, the mixture is allowed to warm to room temperature and held at that temperature for 1 hour. Finally, 500 g of water are introduced into the flask through an addition funnel and the mixture stirred for four hours. The product is washed with a mixture of 1% saline and acetone. Multi-nuclear NMR analysis following solvent removal shows the compound to be $F(CF(CF_3)CF_2O)_nCF(CF_3)CH_2OP(O)[OC_6H_5]_2$.

Example 10
Preparation of a Perfluoroether Phosphate

Into a 500-milliliter 3-neck flask fitted with a mechanical stirrer, thermocouple, and an addition funnel are placed 48.6 g of phenyl dichlorophosphate and 250 g of the alcohol $F(CF(CF_3)CF_2O)_nCF(CF_3)CH_2OH$, prepared according to Example 1b. After all of the reagents are added, the mixture is warmed to about 130° C. for 16 hours and hydrogen chloride is evolved. Finally, following cooling to less than 50° C., 100 g of water are introduced into the flask through an addition funnel and the mixture heated to 95° C. for one hours. The product is washed with a mixture of 1% saline and acetone and residual water removed at 100° C. and 1 mm Hg pressure (133 Pa). Multi-nuclear NMR analysis following solvent removal shows the compound to be $F(CF(CF_3)CF_2O)_nCF(CF_3)CH_2OP(O)[OH][OC_6H_5]$.

TABLE 1

Rust/Corrosion Test Results (Test Method 1)

| Ex. # | Control Test Description | ASTM Method Corrosion Test | | | |
|---|---|---|---|---|---|
| Control Tests with no additive: | | | | | |
| D | Bare pin, no oil | Poor | | | |
| E | Pin and oil, without additive | Poor | | | |

| | | Compatibility with | ASTM Method Corrosion Test Additive Conc.* | | |
|---|---|---|---|---|---|
| Ex. # | Additive Structure | $NaNO_2$* | 0.5% | 1.0% | 2.0% |
| Comparative Examples from the prior art: | | | | | |
| A | $F[CF(CF_3)CF_2O]_{(4-10)}CF(CF_3)CH_2OP[O](OH)_2$ (from Borecki, U.S. Pat. 3,306,855) | Poor | Fair | Fair | Fair |
| B | $\{F[CF(CF_3)CF_2O]_{(4-10)}CF(CF_{3)CH2}O\}_2P[O](OH)_2$ (from Borecki, U.S. Pat. 3,306,855) | Poor | Poor | Poor | Poor |
| C | $F[CF(CF_3)CF_2O]_{(4-10)}CF(CF_3)COOH$ (from Skehan, U.S. 3,367,868) | Poor | NA | NA | Good |
| Examples: | | | | | |
| 1c | $F[CF(CF_3)CF_2O]_{(4-10)}CF(CF_3)CH_2OP[O](OH)(OC_6H_5)$ | Poor | Fair | Good | Excl |
| 2 | $F[CF(CF_3)CF_2O]_{(4-10)}CF(CF_3)CH_2OP[O](ONa)(OC_6H_5)$ | Excl | NA | Excl | Excl |
| 3 | $F[CF(CF_3)CF_2O]_{(4-10)}CF(CF_3)CH_2OP[O](OH)(C_6H_5)$ | Poor | Fair | Good | Excl |
| 4 | $F[CF(CF_3)CF_2O]_{(4-10)}CF(CF_3)CH_2OP[O](ONa)(C_6H_5)$ | Excl | NA | Fair | Fair |
| 5 | $F[CF(CF_3)CF_2O]_{(4-10)}CF(CF_3)CH_2OP[O](OH)(p\text{-}OC_6H_4NO_2)$ | Poor | NA | NA | Excl |
| 6 | $F[CF(CF_3)CF_2O]_{(4-10)}CF(CF_3)CH_2OP[O](OH)(OC_6F_5)$ | Poor | NA | NA | Excl |
| 7 | $F[CF(CF_3)CF_2O]_{(4-10)}CF(CF_3)CH_2OP[O](OH)(p\text{-}OC_6H_4Cl)$ | Poor | NA | NA | Excl |
| 8 | $F(CF_2)_6C_2H_4OP[O](OH)(OC_6H_5)$ | Poor | NA | NA | Excl |
| 9 | $F[CF(CF_3)CF_2O]_{(4-10)}CF(CF_3)CH_2OP[O](OC_6H_5)_2$ | Good | NA | NA | Excl |
| 10 | $F[CF(CT_3)CF_2O]_{4-10)}CF(CF_3)CH_2OP[O](OH)(OC_6H_5)$ | Poor | Fair | Good | Excl. |

*Excl = Excellent, NA = not applicable/not tested.

Table 1 indicates Comparative Examples A to C from the prior art show inferior protection compared with Examples 1c to 10 of the present invention. Examples 1c to 3 and 5 to 10 show excellent performance at the 2% loading. Examples 2, 4, and 9 (sodium salt compositions) show good to excellent compatibility with $NaNO_2$. Immediate rusting occurs with no additives or oil alone (Controls D and E)

In this load-to-failure test, both samples passed the maximum 3,000 lb (1,361 kg) part of the test. However, the improved performance of the oil containing the additive is shown in the reduced torque required. Additionally, the wear scar width measured on the V-block used with the formulated oil was only about 0.5 mm versus a much higher value of about 1.25 mm for the V-block used with the non-

TABLE 2

ASTM-3233 Pin on V-Block Tests (Test Methods 2)

| Sample Description | Load, lb (kg) | Torque, in-lbf (N-m) |
|---|---|---|
| KRYTOX GPL-105 Base Oil | 3,000 (1,361) | 96 (10.8) |
| 2% $F[CF(CF_3)CF_2O]_{(4-10)}CF(CF_3)CH_2OP[O](OH)(OC_6H_5)$ (2% additive from Example 1c) | 3,000 (1,361) | 50 (5.6) | formulated (base) oil. Visually, the pins and V-blocks from the base oil test had acquired a blue-violet color, indicating a high heat flux in the parts. Pins and V-blocks from the test using the oil with the additive of Example 1c, however, were only slightly amber in color, indicating a substantially lower operating temperature during the test.

TABLE 3

4-Ball Wear Test (Test Method 2).

| Sample Description | Wear Scar (mm) |
|---|---|
| DEMNUM S-65 Base Oil | 1.52 |
| F[CF(CF$_3$)CF$_2$O]$_{(4-10)}$CF(CF$_3$)CH$_2$OP[O](OH)(OC$_6$H$_5$) (1% Additive from Example 1c) | 0.66 |

Conditions: immersed in the lubricant, at 75° C. and under a 40 kg load, 1200 rpm for 2 hours, with dry N$_2$ sweep.

Table 3 shows improved wear over the unformulated base oil.

TABLE 4

Cameron-Plint Wear Data (Test Methods 2)

| Sample Description | Wear Scar (mm) |
|---|---|
| DEMNUM S-65 Base Oil | 2.24 |
| 1 % F[CF(CF$_3$)CF$_2$O]$_{(4-10)}$CF(CF$_3$)CH$_2$OP[O](OH)(OC$_6$H$_5$) (1% additive from Example 1c) | 0.89 |

Cameron-Plint oscillatory wear test conditions:
M-50 Steel, 6 mm by 6 mm length pin, Rc60 on
M-50 Steel, 24 mm diameter disk at 150° C.
at 6 Hz with 9 mm stroke length for 2 hours.

Table 4 shows improved wear over the unformulated base oil.

TABLE 5

Micro-Oxidation Stability Results (Test Method 3)

| ° C. | DEMNUM S-65 Base Oil | Additive of Example 1c F[CF(CF$_3$)CF$_2$O]$_{(4-10)}$CF(CF$_3$)CH$_2$OP[O](OH)(OC$_6$H$_5$) |
|---|---|---|
| 290 | Pass | Pass |
| 300 | Fail | Pass |
| 315 | | Pass |
| 330 | | Pass |
| 345 | | Marginal Pass |
| 360 | | Fail |

Table 5 shows a 55° C. improvement in base oil stability using oil formulated with the additive of Example 1c.

What is claimed is:

1. A perfluoropolyether oil or grease containing 0.1 to 10% by weight of an aryl phosphorus compound selected from the group consisting of:
   A. A perfluoropolyether- or perfluoroalkyl-containing and phosphorus-containing compound selected from the group consisting of partially esterified aryl phosphates, aryl phosphonates, and salts thereof, containing either (i) a mono- or poly-alkylene oxide linking group between the phosphorus and a fluorocarbon group, or (ii) no linking group between the phosphorus and fluorocarbon group;
   B. Asymmetrical perfluoropolyether- or perfluoroalkyl-containing and phosphorus-containing compounds being either (i) aryl phosphites or phosphates containing a mono- or poly-alkylene oxide linking group between the phosphorus and a perfluoroether group, or (ii) aryl phosphines, phosphinites, phosphonites, phosphine oxides, phosphinates or phosphonates with no linking group between the phosphorus and a fluorocarbon group;

and combinations thereof wherein said salt is selected from the group consisting of alkali metal salts, alkaline earth metal salts, ammonium salts, and combinations thereof.

2. The perfluoroether oil or grease of claim 1 containing 0.1 to 3% by weight of at least one partially esterified aryl phosphate, aryl phosphonate, or salts thereof, containing either (i) a mono- or poly-alkylene oxide linking group between the phosphorus and a fluorocarbon group, or (ii) no linking group between the phosphorus and fluorocarbon group.

3. The composition of claim 2 wherein said aryl phosphorus compound has the formula of $[Rf—Y—]_{(2-x)}—P(E)—[O_bC_6R_5][OM]_x$ wherein Y is $(CH_2)_{z'}O(CH_2CH_2O)_z$, in which z is 1 to 4 and z' is 0, 1 or 2;

x is 0.05 to 1;

E is oxygen or sulfur, b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf is a polyether chain having a molecular weight ranging from 400 to 15,000 comprising repeating units selected from the group consisting of (1) J—O—(CF(CF$_3$)CF$_2$O)$_o$—(CFXO)$_d$—CFZ—, (2)
J$^1$—O—(CF$_2$CF$_2$O)$_e$—(CF$_2$O)$_f$—CFZ$^1$, (3) J—(CF(CF$_3$)CF$_2$O)$_g$—(CF$_2$CF$_2$O)$_h$—(CFX—O)$_i$—CFZ—, (4) J$^2$—O—(CF(CF$_3$)CF$_2$O)$_j$—CF(CF$_3$)—, (5) J$^3$—O—(CQZ$^2$—CF$_2$CF$_2$—O)$_k$—CQZ$^2$—CF$_2$—, and (6) J$^4$—O—(CF$_2$CF$_2$O)$_l$—CF$_2$—;

J is a fluoroalkyl group selected from the group consisting of —CF$_3$, —C$_2$F$_5$, —C$_3$F$_7$, —CF$_2$Cl, —C$_2$F$_4$Cl, and —C$_3$F$_6$Cl;

X is —F or —CF$_3$;

Z is —F, —Cl, or —CF$_3$;

Z$^1$ is —F or —Cl;

c and d are numbers such that the c/d ratio ranges from 0.01 to 0.5 and the molecular weight ranges from 400 to 15,000;

J$^1$ is a fluoroalkyl group selected from the group consisting of —CF$_3$, —C$_2$F$_5$, —CF$_2$Cl, and —C$_2$F$_4$Cl;

e and f are numbers such that the e/f ratio ranges from 0.5 to 2 and the molecular weight ranges from 400 to 15,000;

g, h and i are numbers such that (g+h) ranges from 1 to 50, the i/(g+h) ratio ranges from 0.1 to 0.05, and the molecular weight is from 400 to 15,000;

$J^2$ is —$C_2F$, or —$C_3F_7$;

j is a number such that the molecular weight ranges from 400 to 15,000;

$J^3$ is selected from the group consisting of —$CF_3$, —$C_2F_5$, and —$C_3F_7$;

Q and $Z^2$, equal or different, are —F, —Cl or —H;

k is a number such that the molecular weight ranges from 400 to 15,000;

$j^4$ is —$CF_3$, or —$C_2F_5$; and l is a number such that the molecular weight ranges from 400 to 15,000.

4. The composition of claim 2 wherein said aryl phosphorus compound has the formula of $[Rf'—Y—]_{(2-x)}$—P(E)—$[O_bC_6R_5][OM]_x$ wherein Y is $(CH_2)_zO(CH_2CH_2O)_{z'}$, in which z is 1 to 4 and z' is 0, 1 or 2;

x is 0.05 to 1;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf' is $Z^2$—$(CF_2)_m$;

$Z^2$ is F, Cl or H; and m has a value from 2 to 20.

5. The composition of claim 2 wherein said aryl phosphorus compound has the formula of $[MO]_x[C_6R_5O_b]$—P(E)—Y—Rf"—Y—P(E)—$[O_bC_6R_5]_{(2-x)}[OM]_x$ wherein Y is $(CH_2)_zO(CH_2CH_2O)_{z'}$, in which z is 1 to 4 and z' is 0, 1 or 2;

x is 0.05 to 1;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf" is a perfluoropolyether chain having a number average molecular weight of 500 to 15,000, selected from the group consisting of (i) —$(CF_2CF_2O)_n$—$(CF_2O)_o$—$CF_2$—, (ii) —$(C_3F_6O)_p$—$(CF_2CF_2O)_q$—$(CFXO)_r$—$CF_2$—, and (iii) —$((CQZ^2)CF_2CF_2O)_s$—$CF_2$—$CF_2$—;

the units with formulae $C_2F_4O$ and $CF_2O$ are randomly distributed along the chain;

n and o are integers, whose ratio, n/o, is in the range of from 0.3 to 5;

p, q and r are numbers such that (p+q) ranges from 1 to 50, and the r/(p+q) ratio ranges from 0.1 to 0.05, and the molecular weight is from 400 to 15,000

X is F or $CF_3$;

Q and $Z^2$, equal or different, are —F, —Cl or —H; and s is a number such that the molecular weight ranges from 400 to 15,000.

6. The composition of claim 2 wherein said aryl phosphorus compound has the formula of $[Rf—]_{(2-x)}$—P(E)—$[O_bC_6R_5][OM]_x$ wherein x is 0.05 to 1;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf is a polyether chain having a molecular weight ranging from 400 to 15,000 comprising repeating units selected from the group consisting of (1) J—O—$(CF(CF_3)CF_2O)_c$—$(CFXO)_d$—CFZ—, (2) $J^1$—O—$(CF_2CF_2O)_e$—$(CF_2O)_f$—$CFZ^1$, (3) J—$(CF(CF_3)CF_2O)_g$—$(CF_2CF_2O)_h$—$(CFX—O)_i$—CFZ—, (4) $J^2$—O—$(CF(CF_3)CF_2O)_j$—$CF(CF_3)$—, (5) $J^3$—O—$(CQZ^2$—$CF_2CF_2$—$O)_k$—$CQZ^2$—$CF_2$—, and (6) $J^4$—O—$(CF_2CF_2O)_l$—$CF_2$—;

J is a fluoroalkyl group selected from the group consisting of —$CF_3$, —$C_2F_5$, —$C_3F_7$, —$CF_2Cl$, —$C_2F_4Cl$, and —$C_3F_6Cl$;

X is —F or —$CF_3$;

Z is —F, —Cl, or —$CF_3$;

$Z^1$ is —F or —Cl;

c and d are numbers such that the c/d ratio ranges from 0.01 to 0.5 and the molecular weight ranges from 400 to 15,000;

$J^1$ is a fluoroalkyl group selected from the group consisting of —$CF_3$, —$C_2F_5$, —$CF_2Cl$, and —$C_2F_4Cl$;

e and f are numbers such that the e/f ratio ranges from 0.5 to 2 and the molecular weight ranges from 400 to 15,000;

g, h and i are numbers such that (g+h) ranges from 1 to 50, the i/(g+h) ratio ranges from 0.1 to 0.05, and the molecular weight is from 400 to 15,000;

$J^2$ is —$C_2F_5$ or —$C_3F_7$;

j is a number such that the molecular weight ranges from 400 to 15,000;

$J^3$ is selected from the group consisting of —$CF_3$, —$C_2F_5$, and —$C_3F_7$;

Q and $Z^2$, equal or different, are —F, —Cl or —H;

k is a number such that the molecular weight ranges from 400 to 15,000;

$J^4$ is —$CF^3$, or —$C_2F_5$; and l is a number such that the molecular weight ranges from 400 to 15,000.

7. The composition of claim 2 wherein said aryl phosphorus compound has the formula of $[Rf—]_{(2-x)}$—P(E)—$[O_bC_6R_5][OM]_x$ wherein x is 0.05 to 1;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf' is $Z^2$—$(CF_2)_m$;

$Z^2$ is —F, —Cl or —H; and m has a value from 2 to 20.

8. The composition of claim 2 wherein said aryl phosphorus compound has the formula of $[MO]_x[C_6R_5O_b]$—P(E)—Rf"—P(E)—$[O_bC_6R_5]_{(2-x)}[OM]_x$ wherein x is 0.05 to 1;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf" is a perfluoropolyether chain having a number average molecular weight of 500 to 15,000, selected from the group consisting of (i) —$(CF_2CF_2O)_n$—$(CF_2O)_o$—$CF_2$—, (ii) —$(C_3F_6O)_p$—$(CF_2CF_2O)_q$—$(CFXO)_r$—$CF_2$—, and (iii) —$((CQZ^2)CF_2CF_2O)_s$—$CF_2$—$CF_2$—;

the units with formulae $C_2F_4O$ and $CF_2O$ are randomly distributed along the chain;

n and o are integers, whose ratio, n/o, is in the range of from 0.3 to 5;

p, q and r are numbers such that (p+q) ranges from 1 to 50, and the r/(p+q) ratio ranges from 0.1 to 0.05, and the molecular weight is from 400 to 15,000;

X is —F or —$CF_3$;

Q and $Z^2$, equal or different, are —F, —Cl or —H; and s is a number such that the molecular weight ranges from 400 to 15,000.

9. The perfluoropolyether oil or grease composition of claim 1 containing 0.1 to 3% by weight of at least one asymmetrical perfluoropolyether- or perfluoroalkyl-containing and phosphorus-containing compound being either (i) aryl phosphites or phosphates containing a mono- or poly-alkylene oxide linking group between the phosphorus and a perfluoroether group, or (ii) aryl phosphines, phosphinites, phosphonites, phosphine oxides, phosphinates or phosphonates with no linking group between the phosphorus and a fluorocarbon group.

10. The composition of claim 9 wherein said aryl phosphorus compound has the formula of $[Rf—Y—]_{(3-y)}$—$P(E)_a$—$[O—C_6R_5]_y$ wherein Y is $(CH_2)_zO(CH_2CH_2O)_{z'}$, in which z is 1 to 4 and z' is 0, 1 or 2;

E is oxygen or sulfur;

each R is independently selected from the group consisting of hydrogen, halogen, alkyl, aryl, nitro, cyano, alkoxy, primary and secondary amino, sulfonyl, carboxyl, and phenoxy;

Rf is a polyether chain having a molecular weight ranging from 400 to 15,000 comprising repeating units selected from the group consisting of (1) J—O—$(CF(CF_3)CF_2O)_c$—$(CFXO)_d$—$CFZ$—, (2) $J^1$—O—$(CF_2CF_2O)_e$—$(CF_2O)_f$—$CFZ^1$, (3) J—$(CF(CF_3)CF_2O)_g$—$(CF_2CF_2O)_h$—$(CFX—O)_i$—$CFZ$—; (4) $J^2$—O—$(CF(CF_3)CF_2O)_j$—$CF(CF_3)$—, (5) $J^3$—O—$(CQZ^2—CF_2CF_2—O)_k$—$CQZ^2$—$CF_2$—, and (6) $J^4$—O—$(CF_2CF_2O)_l$—$CF_2$—;

J is a fluoroalkyl group selected from the group consisting of —$CF_3$, —$C_2F_5$, —$C_3F_7$, —$CF_2Cl$, —$C_2F_4Cl$, and —$C_3F_6Cl$;

X is —F or —$CF_3$;

Z is —F, —Cl, or —$CF_3$;

$Z^1$ is —F or —Cl;

c and d are numbers such that the c/d ratio ranges from 0.01 to 0.5, and the molecular weight ranges from 400 to 15,000;

$J^1$ is a fluoroalkyl group selected from the group consisting of —$CF_3$, —$C_2F_5$, —$CF_2Cl$, and —$C_2F_4Cl$;

e and f are numbers such that the e/f ratio ranges from 0.5 to 2 and, the molecular weight ranges from 400 to 15,000;

g, h and i are numbers such that (g+h) ranges from 1 to 50, the i/(g+h) ratio ranges from 0.1 to 0.05, and the molecular weight is from 400 to 15,000;

$J^2$ is —$C_2F_5$ or —$C_3F_7$;

j is a number such that the molecular weight ranges from 400 to 15,000;

$J^3$ is selected from the group consisting of —$CF_3$, —$C_2F_5$, and —$C_3F_7$;

Q and $Z^2$, equal or different, are —F, —Cl or —H;

k is a number such that the molecular weight ranges from 400 to 15,000;

$J^4$ is —$CF_3$, or —$C_2F_5$;

l is a number such that the molecular weight ranges from 400 to 15,000;

y is 0.05 to 2; and a is 0 or 1.

11. The composition of claim 9 wherein said aryl phosphorus compound has the formula of $(C_6R_5O)_2$—$P(E)_a$—Y—Rf"—Y—$P(E)_a$—$(OC_6R_5)_2$ wherein Y is $(CH_2)_z$—$O(CH_2CH_2O)_{z'}$—, in which z is 1 to 4 and z' is 0, 1 or 2;

E is oxygen or sulfur;

each R is independently selected from the group consisting of hydrogen, halogen, alkyl, aryl, nitro, cyano, alkoxy, primary and secondary amino, sulfonyl, carboxyl, and phenoxy;

Rf" is a perfluoropolyether chain having a number average molecular weight of 500 to 15,000, selected from the group consisting of (i) —$(CF_2CF_2O)_n$—$(CF_2O)_o$—$CF_2$—, (ii) —$(C_3F_6O)_p$—$(CF_2CF_2O)_q$—$(CFXO)_r$—$CF_2$—, and (iii) —$((CQZ^2)CF_2CF_2O)_s$—$CF_2$—$CF_2$—;

the units with formulae $C_2F_4O$ and $CF_2O$ are randomly distributed along the chain;

n and o are integers, whose ratio, n/o, is in the range of from 0.3 to 5;

p, q and r are numbers such that (p+q) ranges from 1 to 50, and the r/(p+q) ratio ranges from 0.1 to 0.05, and the molecular weight is from 400 to 15,000;

X is —F or —$CF_3$;

Q and $Z^2$, equal or different, are —F, —Cl or —H;

s is a number such that the molecular weight ranges from 400 to 15,000; and a is 0 or 1.

12. The composition of claim 9 wherein said aryl phosphorus compound has the formula of $[Rf]_{(3-y)}$—$P(E)_a$—$[O_bC_6R_5]_y$ wherein E is oxygen or sulfur;

b is 0 or 1;

Rf is a polyether chain having a molecular weight ranging from 400 to 15,000 comprising repeating units selected from the group consisting of (1) J—O—(CF(CF$_3$)CF$_2$O)$_c$—(CFXO)$_d$—CFZ—, (2) J$^1$—O—(CF$_2$CF$_2$O)$_e$—(CF$_2$O)$_f$—CFZ$^1$, (3) J—(CF(CF$_3$)CF$_2$O)$_g$—(CF$_2$CF$_2$O)$_h$—(CFX—O)$_i$—CFZ—; (4) J$^2$—O—(CF(CF$_3$)CF$_2$O)$_j$—CF(CF$_3$)—, (5) J$^3$—O—(CQZ$^2$—CF$_2$CF$_2$—O)$_k$—CQZ$^2$—CF$_2$—, and (6) J$^4$—O—(CF$_2$CF$_2$O)$_l$—CF$_2$—;

J is a fluoroalkyl group selected from the group consisting of —CF$_3$, —C$_2$F$_5$, —C$_3$F$_7$, —CF$_2$Cl, —C$_2$F$_4$Cl, and —C$_3$F$_6$Cl;

X is —F or —CF$_3$;

Z is —F, —Cl, or —CF$_3$;

Z$^1$ is —F or —Cl;

c and d are numbers such that the c/d ratio ranges from 0.01 to 0.5 and the molecular weight ranges from 400 to 15,000;

J$^1$ is a fluoroalkyl group selected from the group consisting of —CF$_3$, —C$_2$F$_5$, —CF$_2$Cl, and —C$_2$F$_4$Cl;

e and f are numbers such that the e/f ratio ranges from 0.5 to 2 and the molecular weight ranges from 400 to 15,000; g, h and i are numbers such that (g+h) ranges from 1 to 50, the i/(g+h) ratio ranges from 0.1 to 0.05, and the molecular weight is from 400 to 15,000;

J$^2$ is —C$_2$F$_5$ or —C$_3$F$_7$;

j is a number such that the molecular weight ranges from 400 to 15,000;

J$^3$ is selected from the group consisting of —CF$_3$, —C$_2$F$_5$, and —C$_3$F$_7$;

Q and Z$^2$, equal or different, are —F, —Cl or —H;

k is a number such that the molecular weight ranges from 400 to 15,000;

J$^4$ is —CF$_3$, or —C$_2$F$_5$;

l is a number such that the molecular weight ranges from 400 to 15,000;

y is 0.05 to 2; and a is 0 or 1.

13. The composition of claim 9 wherein said aryl phosphorus compound has the formula of [Rf']$_{(3-y)}$—P(E)$_a$—[O$_b$C$_6$R$_5$]$_y$ wherein E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

Rf' is Z$^2$—(CF$_2$)$_m$;

Z$^2$ is F, Cl or H;

m has a value from 2 to 20;

y is 0.05 to 2; and a is 0 or 1.

14. The composition of claim 9 wherein said aryl phosphorus compound has the formula of [C$_6$R$_5$O]$_2$—P(E)$_a$—Rf"—P(E)$_a$—[O—C$_6$R$_5$]$_2$ wherein E is oxygen or sulfur;

each R is independently selected from the group consisting of hydrogen, halogen, alkyl, aryl, nitro, cyano, alkoxy, primary and secondary amino, sulfonyl, carboxyl, and phenoxy;

Rf" is a perfluoropolyether chain having a number average molecular weight of 500 to 15,000, selected from the group consisting of (i) —(CF$_2$CF$_2$O)$_n$—(CF$_2$O)$_o$—CF$_2$—, (ii) —(C$_3$F$_6$O)$_p$—(CF$_2$CF$_2$O)$_q$—(CFXO)$_r$—CF$_2$—, and (iii) —((CQZ$^2$)CF$_2$CF$_2$O)$_s$—CF$_2$—CF$_2$—;

the units with formulae C$_2$F$_4$O and CF$_2$O are randomly distributed along the chain;

n and o are integers, whose ratio, n/o, is in the range of from 0.3 to 5;

p, q and r are numbers such that (p+q) ranges from 1 to 50, and the r/(p+q) ratio ranges from 0.1 to 0.05, and the molecular weight is from 400 to 15,000;

s is a number such that the molecular weight ranges from 400 to 15,000;

X is —F or —CF$_3$;

Q and Z$^2$, equal or different, are —F, —Cl or —H;

y is 0.05 to 2; and a is 0 or 1.

15. The composition of claim 9 wherein said aryl phosphorus compound has the formula of [Rf'"—C$_6$R$_4$—O]$_{(3-u-w)}$—P(E)—[O$_b$—C$_6$R'$_5$]$_w$[OM']$_u$ wherein Rf'" is Rf' or Rf";

M' is an alkali metal, alkaline earth metal, or ammonium;

u and w are the same or different and are between 0 and 1;

R' is an aryl group;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

Rf' is Z$^2$—(CF$_2$)$_m$;

m has a value from 2 to 20;

Rf" is a perfluoropolyether chain having a number average molecular weight of 500 to 15,000, selected from the group consisting of (i) —(CF$_2$CF$_2$O)$_n$—(CF$_2$O)$_o$—CF$_2$—, (ii) —(C$_3$F$_6$O)$_p$—(CF$_2$CF$_2$O)$_q$—(CFXO)$_r$—CF$_2$—, and (iii) —((CQZ$^2$)CF$_2$CF$_2$O)$_s$—CF$_2$—CF$_2$—;

the units with formulae C$_2$F$_4$O and CF$_2$O are randomly distributed along the chain;

n and o are integers, whose ratio, n/o, is in the range of from 0.3 to 5;

p, q and r are numbers such that (p+q) ranges from 1 to 50, and the r/(p+q) ratio ranges from 0.1 to 0.05, and the molecular weight is from 400 to 15,000;

s is a number such that the molecular weight ranges from 400 to 15,000;

X is —F or —CF$_3$; and

Q and Z$^2$, equal or different, are F, Cl or H.

16. A perfluoropolyether oil or grease composition of containing 0.1 to 3% by weight of at least one salts of a partially esterified aryl phosphates having an aryl group between the phosphorus and a fluorocarbon; said aryl phosphorus compound has the formula of [Rf'"—C$_6$R$_4$—O]$_{(3-u-w)}$—P(E)—[O$_b$—C$_6$R'$_5$]$_w$[OM']$_u$ wherein Rf'" is Rf or Rf";

M' is an alkali metal, alkaline earth metal, or ammonium;

u and w are the same or different and are between 0 and 1;

R' is an aryl group;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

Rf' is $Z^2-(CF_2)_m$;

m has a value from 2 to 20;

Rf" is a perfluoropolyether chain having a number average molecular weight of 500 to 15,000, selected from the group consisting of (i) $-(CF_2CF_2O)_n-(CF_2O)_o-CF_2-$, (ii) $-(C_3F_6O)_p-(CF_2CF_2O)_q-(CFXO)_rCF_2-$, and (iii) $-((CQZ^2)CF_2CF_2O)_s-CF_2-CF_2-$;

the units with formulae $C_2F_4O$ and $CF_2O$ are randomly distributed along the chain;

n and o are integers, whose ratio, n/o, is in the range of from 0.3 to 5;

p, q and r are numbers such that (p+q) ranges from 1 to 50, and the r/(p+q) ratio ranges from 0.1 to 0.05, and the molecular weight is from 400 to 15,000;

s is a number such that the molecular weight ranges from 400 to 15,000;

X is $-F$ or $-CF_3$; and

Q and $Z^2$, equal or different, are F, Cl or H.

17. A perfluoropolyether- or perfluoroalkyl-containing and phosphorus-containing compound selected from the group consisting of partially esterified aryl phosphates, aryl phosphonates, and salts thereof, containing either (i) a mono- or poly-alkylene oxide linking group between the phosphorus and a fluorocarbon group, or (ii) no linking group between the phosphorus and fluorocarbon group wherein said salt is selected from the group consisting of alkali metal salts, alkaline earth metal salts, ammonium salts, and combinations thereof.

18. Compounds of claim 17 having the formula of $[Rf-Y-]_{(2-x)}-P(E)-[O_bC_6R_5][OM]_x$ wherein Y is $(CH_2)_zO(CH_2CH_2O)_{z'}$, in which z is 1 to 4 and z' is 0, 1 or 2;

x is 0.05 to 1;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf is a polyether chain having a molecular weight ranging from 400 to 15,000 comprising repeating units selected from the group consisting of (1) $J-O-(CF(CF_3)CF_2O)_c-(CFXO)_d-CFZ-$, (2) $J^1-O-(CF_2CF_2O)_e-(CF_2O)_f-CFZ^1$, (3) $J-(CF(CF_3)CF_2O)_g-(CF_2CF_2O)_h-(CFX-O)_i-CFZ-$, (4) $J_2-O-(CF(CF_3)CF_2O)_j-CF(CF_3)-$, (5) $J^3-O-(CQZ^2-CF_2CF_2-O)_k-CQZ^2-CF_2-$, and (6) $J^4-O-(CF_2CF_2O)_l-CF_2-$;

J is a fluoroalkyl group selected from the group consisting of $-CF_3$, $-C_2F_5$, $-C_3F_7$, $-CF_2Cl$, $-C_2F_4Cl$, and $-C_3F_6Cl$;

X is $-F$ or $-CF_3$;

Z is $-F$, $-Cl$, or $-CF_3$;

$Z^1$ is $-F$ or $-Cl$;

c and d are numbers such that the c/d ratio ranges from 0.01 to 0.5 and the molecular weight ranges from 400 to 15,000;

$J^1$ is a fluoroalkyl group selected from the group consisting of $-CF_3$, $-C_2F_5$, $-CF_2Cl$, and $-C_2F_4Cl$;

e and f are numbers such that the e/f ratio ranges from 0.5 to 2 and the molecular weight ranges from 400 to 15,000;

g, h and i are numbers such that (g+h) ranges from 1 to 50, the i/(g+h) ratio ranges from 0.1 to 0.05, and the molecular weight is from 400 to 15,000;

$J^2$ is $-C_2F_5$ or $-C_3F_7$;

j is a number such that the molecular weight ranges from 400 to 15,000;

$J^3$ is selected from the group consisting of $-CF_3$, $-C_2F_5$, and $-C_3F_7$;

Q and $Z^2$, equal or different, are $-F$, $-Cl$ or $-H$;

k is a number such that the molecular weight ranges from 400 to 15,000;

$J^4$ is $-CF_3$, or $-C_2F_5$; and l is a number such that the molecular weight ranges from 400 to 15,000.

19. Compounds of claim 17 having the formula of $[Rf-Y-]_{(2-x)}-P(E)-[O_bC_6R_5][OM]_x$ wherein Y is $(CH_2)_zO(CH_2CH_2O)_{z'}$, in which z is 1 to 4 and z' is 0, 1 or 2;

x is 0.05 to 1;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf' is $Z^2-(CF_2)_m$;

$Z^2$ is F, Cl or H; and m has a value from 2 to 20.

20. Compounds of claim 17 having the formula of $[MO]_x[C_6R_5O_b]-P(E)-Y-Rf"-Y-P(E)-[O_bC_6R_5]_{(2-x)}[OM]_x$ wherein Y is $(CH_2)_zO(CH_2CH_2O)_{z'}$, in which z is 1 to 4 and z' is 0, 1 or 2;

x is 0.05 to 1;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf" is a perfluoropolyether chain having a number average molecular weight of 500 to 15,000, selected from the group consisting of (i) $-(CF_2CF_2O)_n-(CF_2O)_o-CF_2-$, (ii) $-(C_3F_6O)_p-(CF_2CF_2O)_q-(CFXO)_r-CF_2-$, and (iii) $-((CQZ^2)CF_2CF_2O)_s-CF_2-CF_2-$;

the units with formulae $C_2F_4O$ and $CF_2O$ are randomly distributed along the chain;

n and o are integers, whose ratio, n/o, is in the range of from 0.3 to 5;

p, q and r are numbers such that (p+q) ranges from 1 to 50, and the r/(p+q) ratio ranges from 0.1 to 0.05, and the molecular weight is from 400 to 15,000;

X is F or $CF_3$;

Q and $Z^2$, equal or different, are —F, —Cl or —H; and s is a number such that the molecular weight ranges from 400 to 15,000.

21. Compounds of claim 17 having the formula of $[Rf—]_{(2-x)}—P(E)—[O_bC_6R_5][OM]_x$ wherein x is 0.05 to 1;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf is a polyether chain having a molecular weight ranging from 400 to 15,000 comprising repeating units selected from the group consisting of (1) $J—O—(CF(CF_3)CF_2O)_o—(CFXO)_d—CFZ—$, (2) $J^1—O—(CF_2CF_2O)_e—(CF_2O)_f CFZ^1$, (3) $J—(CF(CF_3)CF_2O)_g—(CF_2CF_2O)_h—(CFX—O)_i—CFZ—$, (4) $J^2—O—(CF(CF_3)CF_2O)_j—CF(CF_3)—$, (5) $J^3—O—(CQZ^2—CF_2CF_2—O)_k—CQZ^2—CF_2—$, and (6) $J^4—O—(CF_2CF_2O)_1—CF_2—$;

J is a fluoroalkyl group selected from the group consisting of $—CF_3$, $—C_2F_5$, $—C_3F_7$, $—CF_2Cl$, $—C_2F_4Cl$, and $—C_3F_6Cl$;

X is —F or $—CF_3$;

Z is —F, —Cl, or $—CF_3$;

$Z^1$ is —F or —Cl;

c and d are numbers such that the c/d ratio ranges from 0.01 to 0.5 and the molecular weight ranges from 400 to 15,000;

$J^1$ is a fluoroalkyl group selected from the group consisting of $—CF_3$, $—C_2F_5$, $—CF_2Cl$, and $—C_2F_4Cl$;

e and f are numbers such that the e/f ratio ranges from 0.5 to 2 and the molecular weight ranges from 400 to 15,000;

g, h and i are numbers such that (g+h) ranges from 1 to 50, the i/(g+h) ratio ranges from 0.1 to 0.05, and the molecular weight is from 400 to 15,000;

$J^2$ is $—C_2F_5$ or $—C_3F_7$;

j is a number such that the molecular weight ranges from 400 to 15,000;

$J^3$ is selected from the group consisting of $—CF_3$, $—C_2F_5$, and $—C_3F_7$;

Q and $Z^2$, equal or different, are —F, —Cl or —H;

k is a number such that the molecular weight ranges from 400 to 15,000;

$J^4$ is $—CF_3$, or $—C_2F_5$; and l is a number such that the molecular weight ranges from 400 to 15,000.

22. Compounds of claim 17 having the formula of $[Rf—]_{(2-x)}—P(E)—[O_bC_6R_5][OM]_x$ wherein x is 0.05 to 1;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf' is $Z^2—(CF_2)_m$;

$Z^2$ is —F, —Cl or —H; and m has a value from 2 to 20.

23. Compounds of claim 17 having the formula of $[MO]_x[C_6R_5O_b]—P(E)—Rf"—P(E)—[O_bC_6R_5]_{(2-x)}[OM]_x$ wherein x is 0.05 to 1;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

each M is independently selected from the group consisting of hydrogen, alkali metal, alkaline earth metal, and ammonium;

Rf" is a perfluoropolyether chain having a number average molecular weight of 500 to 15,000, selected from the group consisting of (i) $—(CF_2CF_2O)_n—(CF_2O)_o—CF_2—$, (ii) $—(C_3F_6O)_p—(CF_2CF_2O)_q—(CFXO)_r—CF_2—$, and (iii) $—((CQZ^2)CF_2CF_2O)_s—CF_2—CF_2—$;

the units with formulae $C_2F_4O$ and $CF_2O$ are randomly distributed along the chain;

n and o are integers, whose ratio, n/o, is in the range of from 0.3 to 5;

p, q and r are numbers such that (p+q) ranges from 1 to 50, and the r/(p+q) ratio ranges from 0.1 to 0.05, and the molecular weight is from 400 to 15,000;

X is —F or $—CF_3$;

Q and $Z^2$, equal or different, are —F, —Cl or —H; and s is a number such that the molecular weight ranges from 400 to 15,000.

24. Asymmetrical perfluoropolyether- or perfluoroalkyl-containing and phosphorus-containing compounds being aryl phosphites or phosphates containing a mono- or polyalkylene oxide linking group between the phosphorus and a perfluoroether group.

25. Compounds of claim 24 having the formula of $[Rf—Y—]_{(3-y)}—P(E)_a—[O—C_6R_5]_y$ wherein Y is $(CH_2)_zO(CH_2CH_2O)_{z'}$, in which z is 1 to 4 and z' is 0, 1 or 2;

E is oxygen or sulfur;

each R is independently selected from the group consisting of hydrogen, halogen, alkyl, aryl, nitro, cyano, alkoxy, primary and secondary amino, sulfonyl, carboxyl, and phenoxy;

Rf is a polyether chain having a molecular weight ranging from 400 to 15,000 comprising repeating units selected from the group consisting of (1) $J—O—(CF(CF_3)CF_2O)_c—(CFXO)_d—CFZ—$, (2) $J^1—O—(CF_2CF_2O)_e—(CF_2O)_f—CFZ^1$, (3) $J—(CF(CF_3)CF_2O)_g—(CF_2CF_2O)_h—(CFX—O)_i—CFZ—$; (4) $J^2—O—(CF(CF_3)CF_2O)_j—CF(CF_3)—$, (5) $J^3—O—(CQZ^2—CF_2CF_2—O)_k—CQZ^2—CF_2—$, and (6) $J^4—O—(CF_2CF_2O)_1—CF_2—$;

J is a fluoroalkyl group selected from the group consisting of $—CF_3$, $—C_2F_5$, $—C_3F_7$, $—CF_2Cl$, $—C_2F_4Cl$, and $—C_3F_6Cl$;

X is —F or —$CF_3$;

Z is —F, —Cl, or —$CF_3$;

$Z^1$ is —F or —Cl;

c and d are numbers such that the c/d ratio ranges from 0.01 to 0.5, and the molecular weight ranges from 400 to 15,000;

$J^1$ is a fluoroalkyl group selected from the group consisting of —$CF_3$, —$C_2F_5$, —$CF_2Cl$, and —$C_2F_4Cl$;

e and f are numbers such that the e/f ratio ranges from 0.5 to 2 and, the molecular weight ranges from 400 to 15,000;

g, h and i are numbers such that (g+h) ranges from 1 to 50, the i/(g+h) ratio ranges from 0.1 to 0.05, and the molecular weight is from 400 to 15,000;

$J^2$ is —$C_2F_5$ or —$C_3F_7$;

j is a number such that the molecular weight ranges from 400 to 15,000;

$J^3$ is selected from the group consisting of —$CF_3$, —$C_2F_5$, and —$C_3F_7$;

Q and $Z^2$, equal or different, are —F, —Cl or —H;

k is a number such that the molecular weight ranges from 400 to 15,000;

$J^4$ is —$CF_3$, or —$C_2F_5$;

l is a number such that the molecular weight ranges from 400 to 15,000;

y is 0.05 to 2; and a is 0 or 1.

26. Compounds of claim 24 having the formula of $(C_6R_5O)_2$—$P(E)_a$—Y—Rf"—Y—$P(E)_a$—$(OC_6R_5)_2$ wherein Y is $(CH_2)_zO(CH_2CH_2O)_{z'}$, in which z is 1 to 4 and z' is 0, 1 or 2;

E is oxygen or sulfur;

each R is independently selected from the group consisting of hydrogen, halogen, alkyl, aryl, nitro, cyano, alkoxy, primary and secondary amino, sulfonyl, carboxyl, and phenoxy;

Rf" is a perfluoropolyether chain having a number average molecular weight of 500 to 15,000, selected from the group consisting of (i) —$(CF_2CF_2O)_n$—$(CF_2O)_o$—$CF_2$—, (ii) —$(C_3F_6O)_p$—$(CF_2CF_2O)_q$—$(CFXO)_r$—$CF_2$—, and (iii) —$((CQZ^2)CF_2CF_2O)_s$—$CF_2$—$CF_2$—;

the units with formulae $C_2F_4O$ and $CF_2O$ are randomly distributed along the chain;

n and o are integers, whose ratio, n/o, is in the range of from 0.3 to 5;

p, q and r are numbers such that (p+q) ranges from 1 to 50, and the r/(p+q) ratio ranges from 0.1 to 0.05, and the molecular weight is from 400 to 15,000;

X is —F or —$CF_3$;

Q and $Z^2$, equal or different, are —F, —Cl or —H;

s is a number such that the molecular weight ranges from 400 to 15,000; and a is 0 or 1.

27. Compowuds of claim 24 having the formula of $[Rf]_{(3-y)}$—$P(E)_a$—$[O_bC_6R_5]_y$ wherein E is oxygen or sulfur;

b is 0 or 1;

Rf is a polyether chain having a molecular weight ranging from 400 to 15,000 comprising repeating units selected from the group consisting of (1) J—O—$(CF(CF_3)CF_2O)_c$—$(CFXO)_d$—CFZ—, (2)

$J^1$—O—$(CF_2CF_2O)_e$—$(CF_2O)_f$—$CFZ^1$, (3) J—(CF(CF_3)C_2O)_g$—$(CF_2CF_2O)_h$—$(CFX$—$O)_i$—CFZ—; (4) $J^2$—O—$(CF(CF_3)CF_2O)_j$—$CF(CF_3)$—, (5) $J^3$—O—$(CQZ^2$—$CF_2CF_2$—$O)_k$—$CQZ^2$—$CF_2$—, and (6) $J^4$—O—$(CF_2CF_2O)_l$—$CF_2$—;

J is a fluoroalkyl group selected from the group consisting of —$CF_3$, —$C_2F_5$, —$C_3F_7$, —$CF_2Cl$, —$C_2F_4Cl$, and —$C_3F_6Cl$;

X is —F or —$CF_3$;

Z is —F, —Cl, or —$CF_3$;

$Z^1$ is —F or —Cl;

c and d are numbers such that the c/d ratio ranges from 0.01 to 0.5 and the molecular weight ranges from 400 to 15,000;

$J^1$ is a fluoroalkyl group selected from the group consisting of —$CF_3$, —$C_2F_5$, —$CF_2Cl$, and —$C_2F_4Cl$;

e and f are numbers such that the e/f ratio ranges from 0.5 to 2 and the molecular weight ranges from 400 to 15,000; g, h and i are numbers such that (g+h) ranges from 1 to 50, the i/(g+h) ratio ranges from 0.1 to 0.05, and the molecular weight is from 400 to 15,000;

$J^2$ is —$C_2F_5$ or —$C_3F_7$;

j is a number such that the molecular weight ranges from 400 to 15,000;

$J^3$ is selected from the group consisting of —$CF_3$, —$C_2F_5$, and —$C_3F_7$;

Q and $Z^2$, equal or different, are —F, —Cl or —H;

k is a number such that the molecular weight ranges from 400 to 15,000;

$J^4$ is —$CF_3$, or —$C_2F_5$;

l is a number such that the molecular weight ranges from 400 to 15,000.

y is 0.05 to 2; and a is 0 or 1.

28. Compounds of claim 24 having the formula of $[C_6R_5O]_2$—$P(E)_a$—Rf"—$P(E)_a$—$[O$—$C_6R_5]_2$ wherein E is oxygen or sulfur;

each R is independently selected from the group consisting of hydrogen, halogen, alkyl, aryl, nitro, cyano, alkoxy, primary and secondary amino, sulfonyl, carboxyl, and phenoxy;

Rf" is a perfluoropolyether chain having a number average molecular weight of 500 to 15,000 selected from the group consisting of (i) —$(CF_2CF_2O)_n$—$(CF_2O)_o$—$CF_2$—, (ii) —$(C_3F_6O)_p$—$(CF_2CF_2O)_q$—$(CFXO)_r$—$CF_2$—, and (iii) —$((CQZ^2)CF_2CF_2O)_s$—$CF_2$—$CF_2$—;

the units with formulae $C_2F_4O$ and $CF_2O$ are randomly distributed along the chain;

n and o are integers, whose ratio, n/o, is in the range of from 0.3 to 5;

p, q and r are numbers such that (p+q) ranges from 1 to 50, and the r/(p+q) ratio ranges from 0.1 to 0.05, and the molecular weight is from 400 to 15,000;

s is a number such that the molecular weight ranges from 400 to 15,000;

X is —F or —$CF_3$;

Q and $Z^2$, equal or different, are —F, —Cl or —H; and a is 0 or 1.

29. Salts of partially esterified aryl phosphates having an aryl group between the phosphorus and a fluorocarbon; said salt is selected from the group consisting of alkali metal salts, alkaline earth metal salts, ammonium salts, and combinations thereof and has the formula of [Rf'''—$C_6R_4$—O]$_{(3-u-w)}$—$P(E)$—[O$_b$—$C_6R'_5$]$_w$[OM']$_u$ wherein Rf''' is Rf' or Rf'';

M' is an alkali metal, alkaline earth metal, or ammonium;

u and w are the same or different and are between 0 and 1;

R' is an aryl group;

E is oxygen or sulfur;

b is 0 or 1;

each R is independently selected from the group consisting of hydrogen, halogen, alkyl, aryl, nitro, cyano, alkoxy, primary and secondary amino, sulfonyl, carboxyl, and phenoxy;

Rf' is $Z^2$—$(CF_2)_m$;

m has a value from 2 to 20;

Rf'' is a perfluoropolyether chain having a number average molecular weight of 500 to 15,000, selected from the group consisting of (i) —$(CF_2CF_2O)_n$—$(CF_2O)_o$—$CF_2$—, (ii) —$(C_3F_6O)_p$—$(CF_2CF_2O)_q$—$(CFXO)_r$—$CF_2$—, and (iii) —$((CQZ^2)CF_2CF_2O)_s$—$CF_2$—$CF_2$—;

the units with formulae $C_2F_4O$ and $CF_2O$ are randomly distributed along the chain;

n and o are integers, whose ratio, n/o, is in the range of from 0.3 to 5;

p, q and r are numbers such that (p+q) ranges from 1 to 50, and the r/(p+q) ratio ranges from 0.1 to 0.05, and the molecular weight is from 400 to 15,000;

s is a number such that the molecular weight ranges from 400 to 15,000;

X is —F or —$CF_3$; and

Q and $Z^2$, equal or different, are F, Cl or H.

* * * * *